United States Patent [19]

Motogi et al.

[11] Patent Number: 5,699,807
[45] Date of Patent: Dec. 23, 1997

[54] BLOOD PRESSURE MEASURING SYSTEM

[75] Inventors: Jun Motogi; Yoshio Sakai; Sunao Takeda, all of Tokyo, Japan

[73] Assignee: Nihon Kohden Corporation, Tokyo, Japan

[21] Appl. No.: 507,709

[22] Filed: Jul. 26, 1995

[30] Foreign Application Priority Data

Jul. 26, 1994 [JP] Japan .................................. 6-173027

[51] Int. Cl.⁶ .................................................. A61B 5/02
[52] U.S. Cl. ........................... 128/677; 128/681; 128/687
[58] Field of Search ................................. 128/672, 677, 128/679, 680–686, 688, 687; 364/413.03, 413.02, 413.06

[56] References Cited

U.S. PATENT DOCUMENTS

| 4,633,884 | 1/1987 | Imai et al. | 364/413.02 |
| 4,677,984 | 7/1987 | Sramek | 128/681 |
| 4,736,295 | 4/1988 | Lachiver et al. | 364/413.06 |
| 5,337,751 | 8/1994 | Newell et al. | 128/682 |
| 5,355,890 | 10/1994 | Aquirre et al. | 128/680 |

OTHER PUBLICATIONS

"Journal of Clinical Engineering Nov./Dec. 1994."

*Primary Examiner*—Jennifer Bahr
*Assistant Examiner*—Bryan K. Yarnell
*Attorney, Agent, or Firm*—Sughrue, Mion, Zinn, Macpeak & Seas, PLLC

[57] ABSTRACT

A pressure sensor gathers discrete data representing the pulse amplitude of a pulse wave signal when a cuff pressure is increased and decreased. A RAM stores the discrete data of the pulse amplitude. A CPU processes the discrete data by using a spline function, to thereby generate the data representative of a smooth continuous line passing by points of the pulse amplitude of the discrete data. This process reduces a variation of the pulse amplitude of a pulse wave signal, to thereby minimize a variation of the blood pressure values. An inflection point of the smooth continuous line is used as a diastolic blood pressure value.

17 Claims, 4 Drawing Sheets

BLOOD PRESSURE MEASURING SYSTEM

BACKGROUND OF THE INVENTION

1. Field of the Invention

The present invention relates to a blood pressure measuring system for measuring a blood pressure by using data representative of a continuous line connecting the pulse amplitude of a pulse wave signal that is detected.

2. Related Art

A conventional blood pressure monitor detects a pulse wave representative of a pulsation in an artery in the form of a variation of a pressure in a cuff, for example, and measures a diastolic blood pressure and a systolic blood pressure, and a mean blood pressure by using the cuff pressure variation.

There are proposed many methods for measuring a blood pressure by using the cuff pressure variation. One of the blood pressure measuring methods of this type is disclosed in Published Unexamined Japanese Patent Application No. Sho. 62-72317, entitled "Improved Automatic Systolic Blood Pressure Monitor with Supplementally Increased Data" (U.S. Pat. Nos. 4,638,810 and 4,754,761). In the publication, the monotonously increasing and decreasing pulse amplitude of a detected pulse wave signal are used for calculating a blood pressure. Of the pulse amplitude of the pulse wave signal, the pulse amplitude that are 69% and 55% of the maximum or peak values of the amplitude thereof are selected, and the selected ones are averaged. The resultant average value is used as the diastolic blood pressure necessary for measuring a blood pressure.

As described above, in the conventional blood pressure measuring system is based on the presumption that the specific pulse amplitude, i.e., the monotonously increasing and decreasing pulse amplitude, are treated as the pulse amplitude that define a waveshape of the pulse wave signal. For this reason, it is difficult to form a smooth continuous line connecting the pulse amplitude of the pulse wave signal by correcting the pulse amplitude.

Further, the conventional blood pressure measuring system selects the amplitudes of which the values are each 69% and 55% of the peak value, from among the amplitudes of the pulse wave signal, averages those selected ones, and uses the average value as the diastolic blood pressure necessary for measuring a blood pressure. In other words, the numerical data that are empirically gathered are used for calculating the diastolic blood pressure. For this reason, it is difficult to exactly measure the diastolic blood pressure.

SUMMARY OF THE INVENTION

Accordingly, an object of the present invention is to provide a blood pressure measuring system which can generate the data representative of a smooth continuous line passing by the pulse amplitude of a detected pulse wave signal, and hence minimizes a variation of the blood pressure values caused by a variation of the pulse amplitude of the pulse wave signal, which ensues from a variation of a cuff pressure.

Another object of the present invention is to provide a blood pressure measuring system which can exactly measure a mean blood pressure that takes the maximum value of the amplitude of a pulse wave signal, and a diastolic blood pressure at a inflection point of the smooth continuous line passing by the pulse amplitude of a detected pulse wave signal.

To achieve the above objects, there is provided a blood pressure measuring system for measuring a blood pressure by using a pulse wave signal representative of a pulsation of the artery of a living body. The blood pressure measuring system comprises: pulse wave detecting means for continuously detecting a pulse wave of the pulse wave signal; storage means for storing data representative of a continuous pulse wave that is outputted from the pulse wave detecting means, the data including discrete data of the pulse amplitude of the pulse wave; and data processing means operating such that the data processing means reads discrete data of the pulse amplitude of the pulse wave from the storage means and processes the discrete data by using a spline function, thereby to generate data representative of a smooth continuous line, and the data processing means processes the data of the smooth continuous line to thereby produce a blood pressure value.

To achieve the second object, the blood pressure measuring system of the present invention is such that the data processing means further processes the data representative of the smooth continuous line to thereby produce a inflection point of the smooth continuous line, a cuff pressure at the inflection point being treated as a diastolic blood pressure value.

The blood pressure measuring system is such that the data processing means processes the discrete data of the pulse amplitude of the pulse wave that is outputted from the pulse wave detecting means, to thereby weight the discrete data.

The blood pressure measuring system of the present invention continuously detects a pulse wave of a living body, and stores the data of the detected pulse wave including discrete data of the pulse amplitude of the pulse wave.

The blood pressure measuring system weights the discrete data of the pulse amplitude of the pulse wave, processes the weighted discrete data by a spline function, and generates data representative of a smooth continuous line based on the discrete data of the pulse amplitude.

Accordingly, the pulse amplitude of the pulse wave signal are corrected, and a smooth continuous line that passes by the points of the actually measured pulse amplitude is formed.

A variation of the blood pressure values caused by a variation of the pulse amplitude of the pulse wave signal, which ensues from a variation of a cuff pressure, is minimized.

According to the present invention, the blood pressure measuring system generates the data of a smooth continuous line by processing the pulse amplitude of the pulse wave signal by a spline function, and further processes the data of a smooth continuous line to find an inflection point of the continuous line. A cuff pressure at the inflection point is used as a diastolic blood pressure value. Accordingly, it is possible to exactly measure a mean blood pressure that takes the maximum value of the amplitude of the pulse wave signal, and a diastolic blood pressure of a cuff pressure that is positioned at the inflection point of the continuous line passing by the pulse amplitude of the pulse wave signal.

DETAILED DESCRIPTION OF THE PREFERRED EMBODIMENTS

The preferred embodiment will be described with reference to the accompanying drawings.

Figure 1:
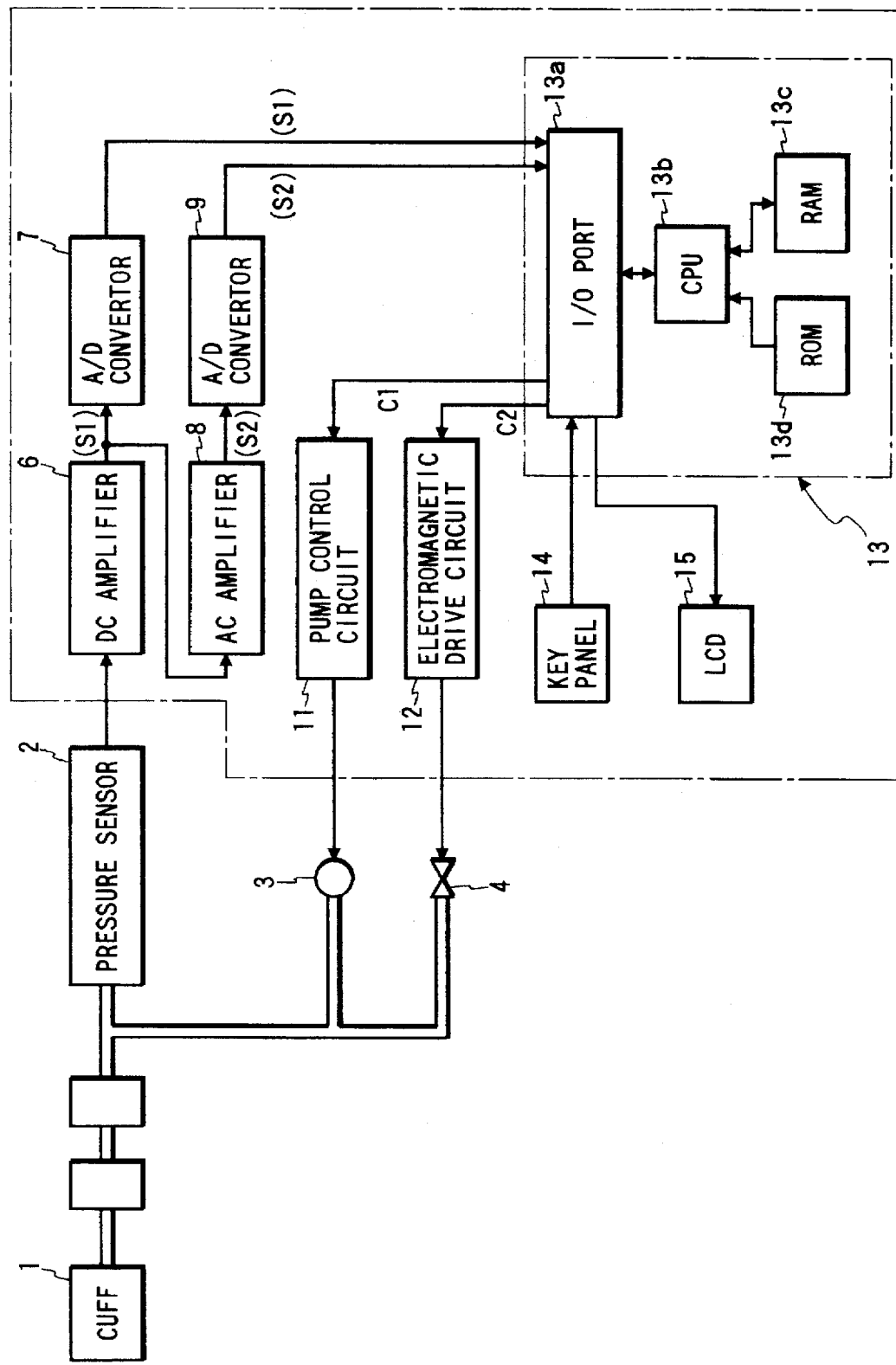
FIG. 1 is a block diagram showing an arrangement of a blood pressure monitor into which a blood pressure measuring system according to the present invention.

FIG. 1 is a block diagram showing an arrangement of a blood pressure device into which a blood pressure measuring system according to the present invention is incorporated. In FIG. 1, the blood pressure monitor includes a cuff 1 put on the upper part of an arm of a subject, a pressure sensor 2 for sensing an air pressure in the cuff 1, and a pump 3 for increasing a pressure up to a value indicated by a control signal C1. The blood pressure monitor further includes an electromagnetic valve 4 for reducing a pressure in the cuff 1 after the increase of the cuff pressure by stepwise discharging the air from the cuff 1 in accordance with a value indicated by a control signal C2, and a DC amplifier 6 for amplifying a DC pressure signal S1 outputted from the pressure sensor 2.

Additionally, the blood pressure monitor includes an A/D convertor 7 for converting a pressure signal S1 outputted from the DC amplifier 6 into a digital signal, and an AC amplifier 8 for amplifying the pressure signal S1 from the DC amplifier 6 and outputting a blood-pressure pulse wave signal S2.

Furthermore, the blood pressure monitor includes an A/D convertor 9 for converting the blood-pressure pulse wave signal S2 from the AC amplifier 8 into a digital signal, a pump control circuit 11 for controlling the flow of air from the pump 3, and an electromagnetic drive circuit 12 for controlling the discharge of air by the electromagnetic valve 4.

A control circuit 13 is further included in the blood pressure monitor. The control circuit 13 executes a smoothing spline process (to be described later) by using the pressure signal S1 and the blood-pressure pulse wave signal S2 from the A/D convertors 7 and 9, computes a diastolic blood pressure after the smoothing spline process is executed, controls the pump 3 by the pump control circuit 11, and controls the pressure reduction by discharging a compressed air from the cuff 1 through the operation of the electromagnetic drive circuit 12.

A key panel 14 for instructing a measurement start, and various controls, and a liquid crystal display (LCD) 15 for displaying the contents of the process, waveforms processed, and the like, are further contained in the blood pressure monitor.

The control circuit 13 is made up of an I/O port 13a, a CPU 13b, and a RAM 13c as a work memory, and a ROM 13d which stores a control program. The I/O port 13a receives the pressure signal S1 and the blood-pressure pulse wave signal S2 from the A/D convertors 7 and 9, and sends control signals to the pump control circuit 11 and the electromagnetic drive circuit 12.

Figure 2:
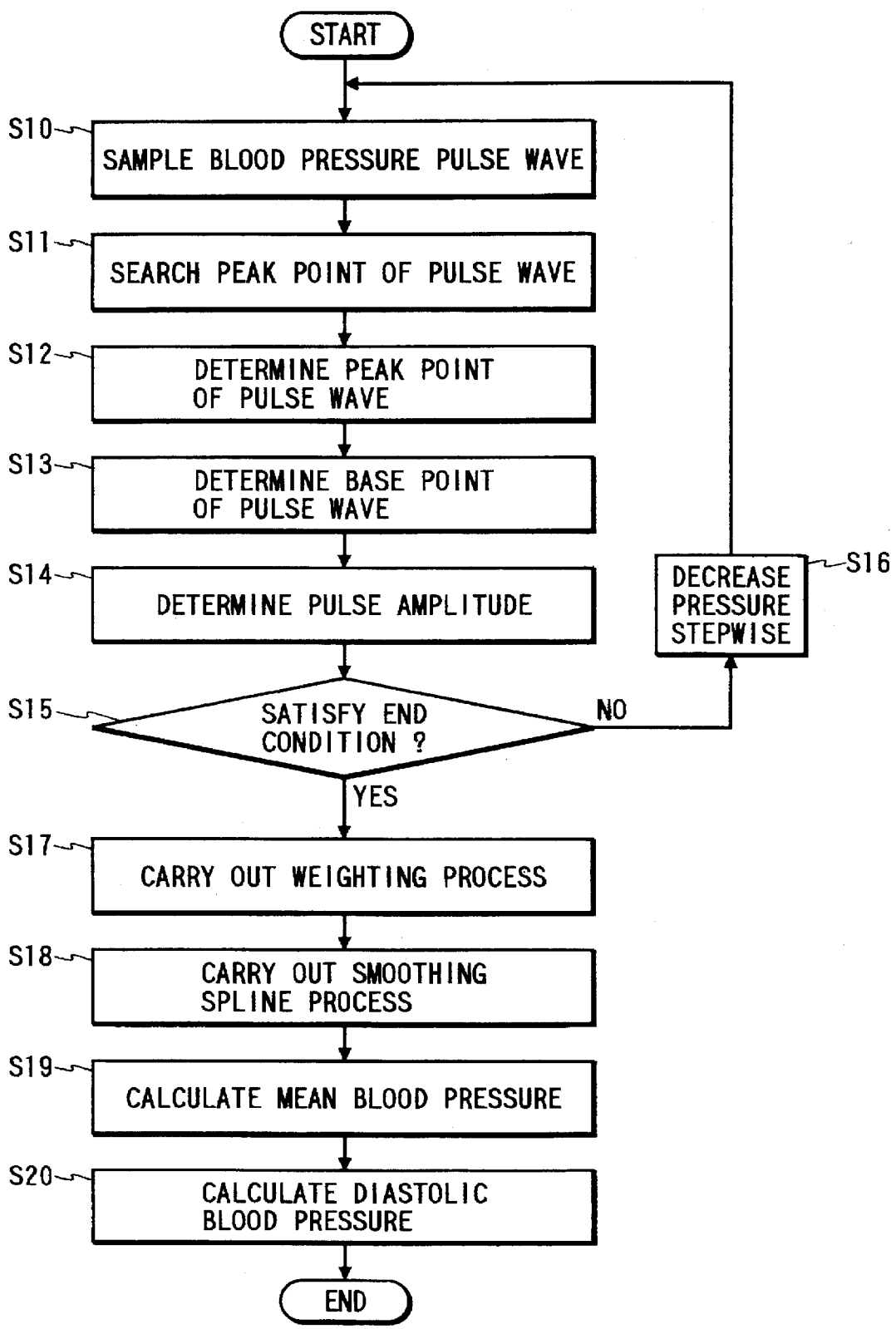
FIG. 2 is a flowchart showing a sequence of procedural steps in the overall operation of the blood pressure monitor shown in FIG. 1.

FIG. 2 is a flowchart showing a sequence of procedural steps in the overall operation (blood pressure measuring operation) of the blood pressure monitor shown in FIG. 1.

Referring to FIGS. 1 and 2, a pressure increase value is set on the key panel 14. The key panel 14 produces a control signal for the set pressure increase value and sends it to the control circuit 13. In response to the control signal, the control circuit 13 controls the pump 3 so as to increase a pressure in the cuff 1 up to the value set on the key panel 14.

Then, the control circuit 13 controls the electromagnetic valve 4 so as to stepwise decrease the pressure in the cuff 1.

The CPU 13b of the control circuit 13 fetches a pressure signal S1 representative of a pressure decreasing state from the pressure sensor 2, through the DC amplifier 6, the A/D convertor 7, and the I/O port 13a.

The CPU 13b fetches a blood-pressure pulse wave signal S2 from the pressure sensor 2, through the DC amplifier 6, the AC amplifier 8, the A/D convertor 9, and the I/O port 13a (step 10 denoted as S10 in the drawing).

The CPU 13b searches the blood-pressure pulse wave signal S2 for the peak value of the amplitudes of the pulse wave signal, and picks it up (S11 and S12).

Further, it determines a base point where a pulse wave starts to rise (S13).

The CPU 13b determines a pulse amplitude of the pulse wave signal, and judges whether or not the amplitude of the blood-pressure pulse wave signal S2 during the course of decreasing the pressure in the cuff 1 satisfies a predetermined condition of ending the pressure decrease (S14 and S15).

In this embodiment, for example, the predetermined end condition means a state that several waves continuously having the pulse amplitude a certain ratio, say 50 to 70% of the peak value of the amplitude are detected.

If the end condition is not satisfied (S15; the answer is NO), the CPU 13b carries out a further pressure decrease, and returns to the step S10. Then, it repeats the sequence of the steps thus far made.

If the end condition is satisfied (S15; the answer is YES), the control circuit 13 directs the electromagnetic drive circuit 12 to open the electromagnetic valve 4 to the full.

The thus far gathered data is stored in the RAM 13c. Then, the control circuit 13 carries out a process of weighting the pulse amplitude of a pulse wave signal during the course of decreasing the pressure in the cuff 1 (S17).

When a subject suddenly moves during the measurement of blood pressure, the pulse amplitude of the pulse wave signal abruptly increases or decreases. In this case, an error of the pulse amplitude must be minimized. It is for this reason that the weighting process is carried out.

There are many weighting methods. One of the weighting methods follows. In this method, all of the pulse amplitude of a pulse wave signal are first weighted, viz., subjected to a first smoothing spline process. By the process, the pulse amplitude of the pulse signal are corrected.

Then, a weighting coefficient is selected for another smoothing spline process. To this end, the pulse amplitude of a pulse wave signal are measured. The corrected pulse amplitude are compared with the measured pulse amplitude in order to find the differences therebetween.

The weighting coefficients are determined depending on the differences of the pulse amplitude.

In this embodiment, when the corrected pulse amplitude is within 10% of the measured pulse amplitude, the weighting coefficient is 1. When the former is within 30% of the latter, the weighting coefficient is 0.5.

A second smoothing spline process of the (2M−1)th degree (M: natural number) is carried out in order to form a continuous line passing by the pulse amplitude of a detected pulse wave signal. In this case, the pulse amplitude corrected by the weighting coefficients are used. The second smoothing spline processes is carried out by the control circuit 13 (FIG. 1) in a step S18 in this embodiment.

Incidentally, the smoothing spline processes is a kind of the spline processes. Of the smoothing spline processes, the smoothing spline processes of the (2M−1)th degree is used in the present embodiment.

The smoothing spline processes is a process for approximating discrete data by a curve that is the smoothest in shape and closest in value to the discrete data. In this process, the curve is formed such that it passes through points where the differences between the curve and the data are the smallest and it is the smoothest in shape as a whole, and it does not always contain data points.

Figure 3:
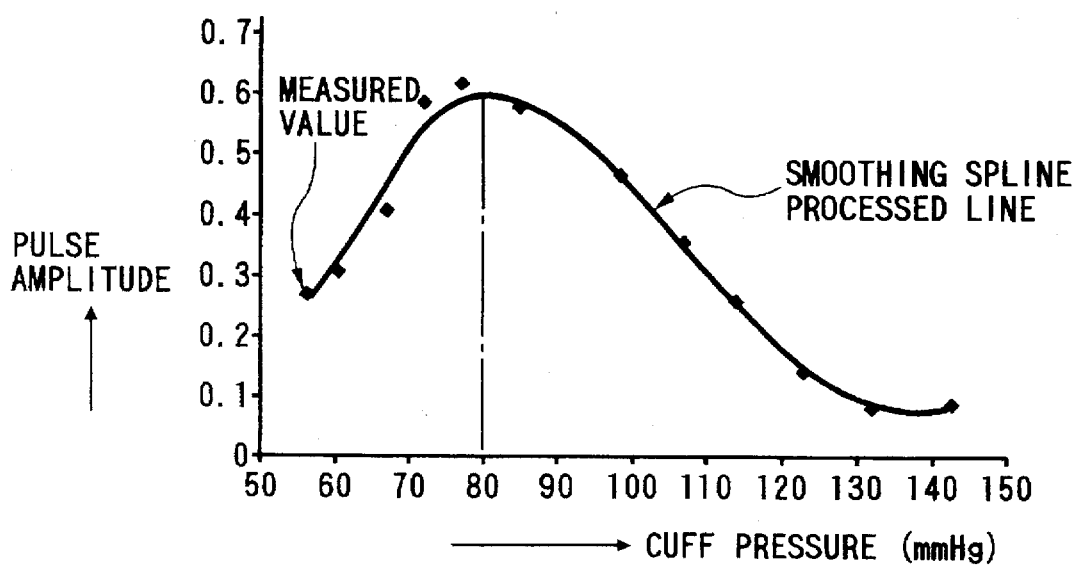
FIG. 3 is a graph showing a smooth continuous line formed by processing the pulse amplitude of a pulse wave signal by a smoothing spline processes, the pulse wave signal being varied with respect to a pressure in the cuff.

FIG. 3 is a graph showing a smooth continuous line formed by processing the pulse amplitude of a pulse wave signal by a smoothing spline processes, the pulse wave signal being varied with respect to a pressure in the cuff.

Discrete data of the pulse amplitude of the pulse wave signal that varies with the increase and decrease of the pressure in the cuff 1 are stored in the RAM 13c. The CPU 13b reads the discrete data out of the RAM 13c, processes the discrete data by using a related spline function, and generates a series of data represented by a smoothed continuous curve that passes by the pulse amplitude of the data.

The series of data are also stored into the RAM 13c. By using the curve thus corrected for the cuff pressure, it is possible to minimize a variation of the blood pressure values that is caused by a variation of the pulse amplitude of a detected pulse wave signal.

Subsequently, a mean blood pressure value is calculated by using data of the smooth continuous line thus formed (S19).

Figure 4:
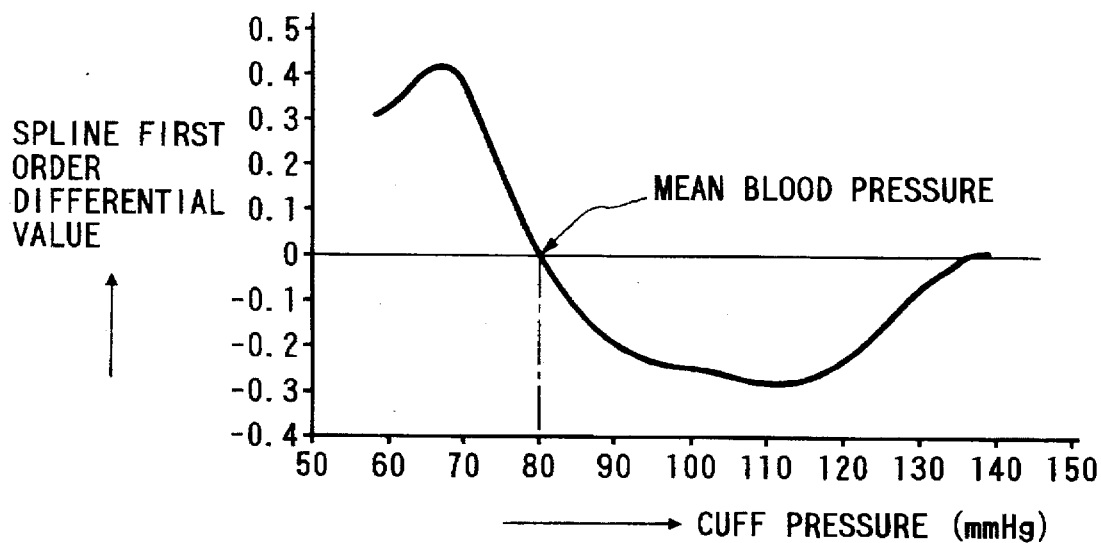
FIG. 4 is a graph useful in explaining the calculation of a mean blood pressure value.

FIG. 4 is a graph useful in explaining the calculation of a mean blood pressure value.

The CPU 13b reads the data of the smooth continuous line (FIG. 3) from the RAM 13c, and processes it by a related first order differential equation.

As shown in FIG. 4, the CPU 13b picks up a value at a point on the differentiated cuff pressure curve where the differentiated value is zero (0), and stores it as a mean blood pressure value into the RAM 13c.

In the next step S20, the CPU 13b calculates a diastolic blood pressure value using the data representative of the smooth continuous line (FIG. 3).

Figure 5:
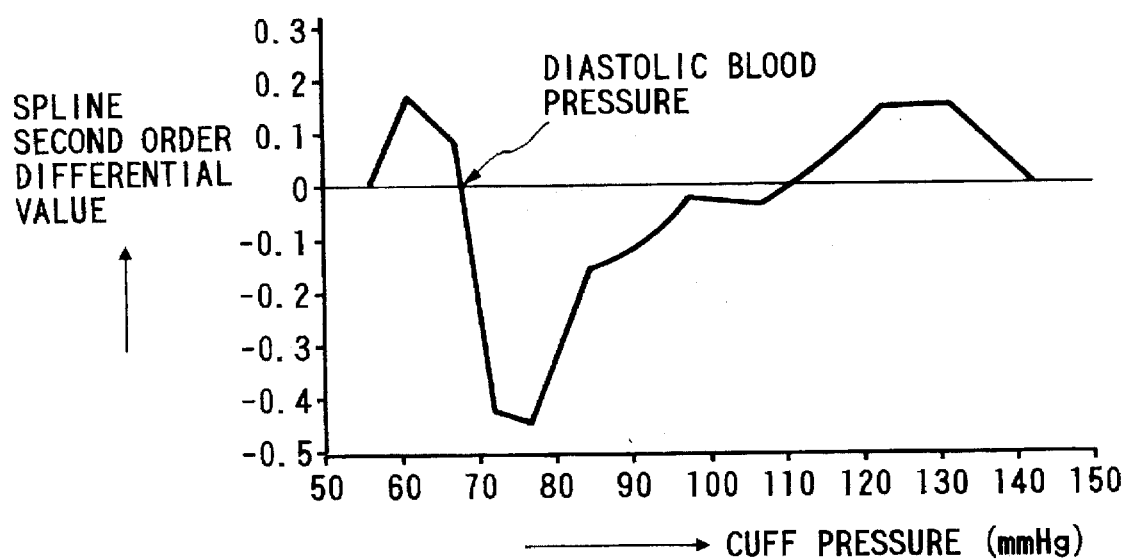
FIG. 5 is a graph useful in explaining the calculation of a diastolic blood pressure value.

FIG. 5 is a graph useful in explaining the calculation of a diastolic blood pressure value.

The CPU 13b reads the data of the smooth continuous line (FIG. 3) from the RAM 13c, and processes it by a related Second order differential equation. The CPU 13b picks up a value at a point on the differentiated cuff pressure curve where the differentiated value is zero (0), and stores it as a diastolic blood pressure value into the RAM 13c.

By the process, one can exactly know an inflection point of the smooth continuous line passing by the actually measured pulse amplitude of the pulse wave signal. In this way, the blood pressure monitor of the embodiment can calculate a diastolic blood pressure value on the basis of the principle of the present invention.

As described above, the blood pressure measuring system continuously detects a pulse wave of a living body, weights discrete data of the pulse amplitude of the pulse wave, processes the weighted discrete data by a spline function, and generates data representative of a smooth continuous line based on the discrete data of the pulse amplitude, thereby correcting the pulse amplitude of the pulse wave signal. Accordingly, a smooth continuous line that passes by the points of the actually measured pulse amplitude values is formed.

A variation of the blood pressure values caused by a variation of the pulse amplitude of the pulse wave signal, which ensues from a variation of a cuff pressure, is minimized.

As a result, it is possible to exactly measure a mean blood pressure and a diastolic blood pressure.

According to the present invention, the blood pressure measuring system generates the data of a smooth continuous line by processing the pulse amplitude of the pulse wave signal by a spline function, and further processes the data of a smooth continuous line to find an inflection point of the continuous line. A cuff pressure at the inflection point is used as a diastolic blood pressure value. Accordingly, the blood pressure monitor of the embodiment can calculate a diastolic blood pressure value on the basis of the principle of the present invention.

What is claimed is:

1. A blood pressure measuring system comprising:
    blood pressure measuring means for measuring a blood pressure by using a pulse wave signal representative of a pulsation of an artery of a living body, said blood pressure measuring means comprising:
        pulse wave detecting means for continuously detecting a pulse wave of said pulse wave signal;
        storage means for storing data representative of a continuous pulse wave that is outputted from said pulse wave detecting means, said data including discrete data of a pulse amplitude of said pulse wave;
        data processing means for reading discrete data of said pulse amplitude of said pulse wave from said storage means, and for processing said discrete data by using a spline function to generate data representative of a smooth continuous line; and
        blood pressure calculating means for calculating a blood pressure value on the basis of said data of said smooth continuous line, said blood pressure calculating means including detecting means for detecting a cuff pressure being treated as a diastolic blood pressure at an inflection point of said data representative of said smooth continuous line.

2. The blood pressure measuring system according to claim 1, further comprising:
    weight processing means for applying a weight processing to said discrete data of said pulse amplitude of said pulse wave that is outputted from said pulse wave detecting means.

3. A blood pressure measuring system as claimed in claim 1, wherein said detecting means performs a second order differentiation on said data representative of said smooth continuous line to achieve said inflection point.

4. A blood pressure measuring method for measuring a blood pressure by using a pulse wave signal representative of a pulsation of an artery of a living body, comprising the steps of
    continuously detecting a pulse wave of said pulse wave signal;
    storing data representative of a continuous pulse wave, said data including discrete data of a pulse amplitude of said pulse wave;
    reading said discrete data of said pulse amplitude of said pulse wave;

processing said discrete data by using a spline function to generate data representative of a smooth continuous line;

calculating a blood pressure value on the basis of said data of said smooth continuous line; and detecting a cuff pressure being treated as a diastolic blood pressure at an inflection point of said data representative of said smooth continuous line.

5. The blood pressure measuring method according to claim 4, further comprising:

applying a weight processing to said discrete data of said pulse amplitude of said pulse wave.

6. A blood pressure measuring method as claimed in claim 4, wherein said detecting step includes the step of performing a second order differentiation on said data represented of said smooth continuous line to achieve said inflection point.

7. A blood pressure measuring system comprising a blood pressure measuring circuit for measuring a blood pressure by using a pulse wave signal representative of a pulsation of an artery of a living body, said blood pressure measuring means comprising:

pulse wave detecting means for continuously detecting a pulse wave of said pulse wave signal;

storage means for storing data representative of a continuous pulse wave that is outputted from said pulse wave detecting means, said data including discrete data of a pulse amplitude of said pulse wave;

correcting means for reading discrete data of said pulse amplitude of said pulse wave from said storage means, and for correcting said discrete data by using a predetermined function to generate corrected data of said pulse amplitude, weighting coefficient determining means for determining weighting coefficient on the basis of a ratio defined by said data read from said storage means and said corrected data, data processing means for weighting said data read from said storage means by said weighting coefficient, and for processing the weighted data using a spline function to generate data representative of a smooth continuous line; and blood pressure calculating means for calculating a blood pressure value on the basis of said smooth continuous line.

8. The blood pressure measuring system according to claim 7, wherein said correcting means includes spline function processing means to generate correcting data by using a spline function.

9. The blood pressure measuring system according to claim 7, wherein said weighting coefficient determining means comprises:

subtraction calculating means for subtracting said corrected data from said data read from said storage means, selecting means for selecting data for weighting on the basis of a ratio defined by said subtracted data provided by said subtraction calculating means and said data read from said storage means; and wherein said data processing means weights data selected by said selecting means by said weighting coefficient.

10. The blood pressure measuring system according to claim 9, wherein said weighting coefficient is 0.5, and wherein said ratio ranges from 10% to 30%.

11. The blood pressure measuring system according to claim 7, wherein said data processing means uses a (2M−1)-th order spline function for generating data representative of a smooth continuous line.

12. The blood pressure measuring system according to claim 7, wherein said blood pressure calculating means includes detecting means for detecting a cuff pressure being treated as a diastolic blood pressure at inflection of said data representative of said smooth continuous line.

13. A method of measuring a blood pressure by using a pulse wave signal representative of a pulsation of an artery of a living body, said method comprising the steps of:

continuously detecting a pulse wave of said pulse wave signal;

storing data representative of said pulse wave being continuously detected, said data including discrete data of a pulse amplitude of said pulse wave;

reading said discrete data of said pulse amplitude of said pulse wave from said stored data;

correcting said discrete data by using a predetermined function to generate corrected data of said pulse amplitude;

determining a weighting coefficient on the basis of a ratio defined by said data read from said stored data and said corrected data;

weighting said data read from said stored data using said weighting coefficient to generate weighted data;

processing the weighted data using a spline function to generate data representative of a smooth continuous line; and calculating a blood pressure value on the basis of said smooth continuous line.

14. The method according to claim 13, wherein said predetermined function is a spline function.

15. The method according to claim 13, wherein said step of determining further comprises the steps of:

subtracting said corrected data from said data read from said stored data to produce subtracted data, and selecting data for weighting on the basis of a ratio defined by said subtracted data and data read during said step of reading; and wherein said step of weighting, data selected during said step of selecting is weighted by said weighting coefficient.

16. The method according to claim 15, wherein said weighting coefficient is 0.5, and wherein said ratio ranges from 10% to 30%.

17. The method according to claim 13, wherein said spline function is a (2M−1)-th order spline function.

* * * * *